United States Patent [19]

Burzynski

[11] Patent Number: 5,646,182
[45] Date of Patent: Jul. 8, 1997

[54] METHODS FOR TREATING AUTOIMMUNE DISEASES

[76] Inventor: Stanislaw R. Burzynski, 20 W. Rivercrest, Houston, Tex. 77042

[21] Appl. No.: 898,295

[22] Filed: Jun. 15, 1992

[51] Int. Cl.⁶ .................. A61K 31/235; A61K 31/195
[52] U.S. Cl. .................. 514/532; 514/544; 514/561
[58] Field of Search .................. 514/532, 544, 514/561

[56] References Cited

U.S. PATENT DOCUMENTS

| | | | |
|---|---|---|---|
| 4,248,892 | 2/1981 | Kanamaru et al. | 424/317 |
| 4,256,766 | 3/1981 | Mori et al. | 424/319 |
| 4,438,029 | 3/1984 | Erickson et al. | |
| 4,439,448 | 3/1984 | Munakata et al. | 424/309 |
| 4,558,057 | 12/1985 | Burzynski. | |
| 4,593,038 | 6/1986 | Burzynski. | |
| 4,826,680 | 5/1989 | Jaeger. | |
| 5,039,704 | 8/1991 | Smith et al. | |
| 5,066,666 | 11/1991 | Ozato et al. | |
| 5,089,508 | 2/1992 | Burzynski. | |
| 5,098,906 | 3/1992 | Sircar et al. | |
| 5,102,883 | 4/1992 | Ackerman et al. | |
| 5,108,999 | 4/1992 | Patterson et al. | |
| 5,116,622 | 5/1992 | Burzynski. | |

FOREIGN PATENT DOCUMENTS 1522212  8/1978  United Kingdom .

OTHER PUBLICATIONS

Burzynski, S.R., "Isolation, Purification, and Synthesis of Antineoplastons," International Journal of Experimental and Clinical Chemotherapy, vol. 2:63–69 (1989).

Burzynski, S.R. et al., "Preclinical Studies on Antineoplaston AS2–1 and Antineoplaston AS2–5," Drugs. Exptl. Clin. Res. Suppl. 1 12:11–16 (1986).

*Primary Examiner*—Marianne M. Cintins
*Assistant Examiner*—M. Moezie
*Attorney, Agent, or Firm*—Arnold, White & Durkee

[57] ABSTRACT

The present invention provides methods for treating autoimmune disease in humans by administering to an afflicted host pharmaceutical compositions containing a therapeutically effective amount of a combination of

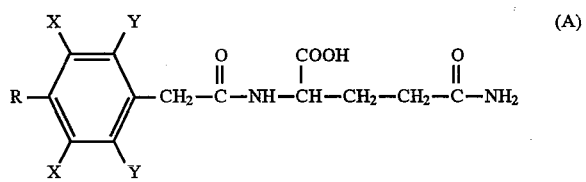

and

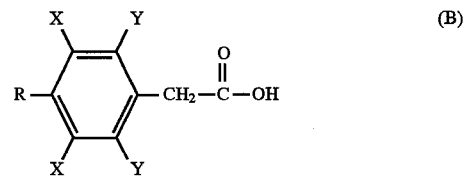

in a weight ratio ranging from about 1:1 to about 1:10 (A:B);
wherein R is OH, $NH_2$, OW, or H;
X is H, F, Cl, Br, I, OH, OW, $NO_2$, or $NH_2$;
Y is H, F, Cl, Br, or I;
W is

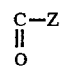

or a $C_1$ to $C_{12}$ aliphatic group;
Z is an aliphatic or aromatic group of $C_1$ to $C_{12}$;
X and Y can both vary within the compound; or pharmaceutically acceptable salts thereof.

Particularly disclosed herein is a composition comprising a 1 to 4 ratio of the sodium salts of phenylacetylglutamine and phenylacetic acid, formulated in both oral and parenteral forms clinically useful in the treatment of rheumatoid arthritis, lupus erythematosus, vasculitis, insulin dependent diabetes mellitus and multiple sclerosis.

20 Claims, No Drawings

METHODS FOR TREATING AUTOIMMUNE DISEASES

FIELD OF THE INVENTION

The present invention relates to the use of phenylacetyl derivatives in the treatment of autoimmune diseases.

BACKGROUND OF THE INVENTION

The field of rheumatology and therapy of autoimmune disease is facing perhaps the biggest revolution since it was established in the mid-nineteenth century. The teachings of the last 35 years are seriously challenged. The treatment pyramid for rheumatoid arthritis (RA) which seemed as stable as pyramids in the Egyptian desert is falling apart. It has been realized that RA is a more serious disease than it was thought of before. It results in higher mortality and disability as our population ages. The potentially serious changes in the joints frequently occur at the beginning of the disease. A number of rheumatologists are now suggesting more aggressive treatments, such as the use of disease-modifying antirheumatic drugs (DMARD). Effective DMARD's are yet to be found. Current disease-modifying treatments usually are less effective within two years.

Regulation of autoimmune response offers an attractive background for the introduction of new DMARD's. Every human organism has the ability to make antibodies against it own cells. Production of antibodies may play an important part in the removal of cellular remnants. Out of approximately 100,000 macromolecules present in the cell, less than 500 are autoantigens. A number of these antigens play a vital part in the synthesis of proteins. It is very important to notice that amino acyl-tRNA synthetases are among these antigens (Mathews, M. B. et al., Nature 304:177 (1983), Mathews, M. B. et al., J. Exp. Med. 160:420 (1984) and Bunn, C. C. et al., J. Exp. Med. 163:1281 (1986)). The autoimmune reaction is sustained because of persistent activation of T-lymphocytes (Sinha, A. A. et al., Science 248:1380 (1990)). The differentiation of T-cells plays a crucial part in cell tolerance. The errors in differentiation of T-cells may result in autoimmune reaction. The present inventor postulates that autoimmune disorders are the diseases of cellular differentiation. The use of differentiation inducers should lead to the remission of the disease, if such hypothesis is true.

Without wishing to bound to any proposed theory, the present inventor postulates that the human body possesses a Biochemical Defense System (BDS) (Burzynski, S. R., Internal. J. Exp. Clin. Chemother. 2:63 (1989)and Burzynski, S. R., 17th Internat. Cong. Chemother., Berlin (1991)). This system parallels the immune defense, but protects the organism against the enemy within the body. The main purpose is no longer the defense against the micro-organism, but defense against defective cells. Chemical components of this biochemical defense system are peptides, amino acid derivatives and organic acids defined as antineoplastons (Burzynski, S. R., Physiol. Chem. Phys. 8:275 (1976) and Burzynski, S. R., U.S. Pat. No. 4,470,970). The mechanism of defense is based not on destruction, but on the reprogramming of defective cells through induction of differentiation.

The research on antineoplastons began in Poland in 1967 (Burzynski, S. R., Experientia 25:490 (1969) and Burzynski, S. R., Drugs Exptl. Clin. Res. Suppl. 1 12:1 (1986)). Initially, the work concentrated on the isolation of peptides which exist in the blood of healthy people and are deficient in cancer patients. Due to the small amount of raw material available for the study, in the following years, antineoplastons were isolated from urine instead of blood. In 1980 the structure of the first antineoplaston was identified and reproduced synthetically (Burzynski, S. R. et al., Proc. 13th Internat. Cong. Chemother., Vienna, Austria 17, P.S. 12. 4. 11-4).

Antineoplastons are divided into two groups. One group contains compounds which have a wide spectrum of activity and includes Antineoplaston A1, A2, A3, A4, A5, A10, AS2-1, AS2-5. Antineoplastons A1, A2, A3, A4 and A5 contain peptides isolated from urine and Antineoplaston A10, AS2-1 and AS2-5 are the synthetic products. See e.g. U.S. Pat. Nos. 4,470,970, 4,558,057 and 4,559,325. In addition to the first group, there are antineoplastons that are active against a single specific type of neoplasm, such as Antineoplaston H, L and O. Antineoplaston A10 is the first active ingredient isolated and reproduced by synthesis. Acid hydrolysis of Antineoplaston A10 initially produces phenylacetylglutamine and phenylacetylisoglutamine. When hydrolysis is carried further, the products of reaction include phenylacetic acid, glutamic acid and ammonia. The sodium salt of phenylacetylglutamine was named Antineoplaston AS2-5 and the mixture of the sodium salts of phenylacetylglutamine and phenylacetic acid in the ratio of 1:4 was named Antineoplaston AS2-1 (Burzynski, S. R. et al., Drugs Exptl. Clin. Res. Suppl. 1 12:11 (1986)).

According to the present inventor, AS2-1 seems to induce differentiation by reducing the level of glutamine in cells and substituting glutamine with phenylacetylglutamine. Relative excess of glutamine is essential for entering S-phase of cell cycle (Zetterberg, A. et al., Cell Physiol. Chem. 108:365 (1981)). In Swiss 3T3 cells cultured and starved to quiescence, a relative excess of glutamine is necessary for approximately seven hours from the end of $G_o$ to the beginning of S phase (Zetterberg, A. et al., Cell Physiol. Chem. 108:365 (1981)).

The availability of glutamine for cells in the human organism is regulated through the well-known reaction of the conjugation of glutamine with phenylacetic acid to phenylacetylglutamine (Thierfelder, H. et al., Z. Physiol. Chem. 94:1 (1915)). Phenylacetic acid is produced in substantial amounts in the human body and over 90% is bound with glutamine to form phenylacetylglutamine (Seakins, J. W. T., Clin. Chem. Acta. 35:121 (1971)). The type of amino acid conjugated with phenylacetic acid is different for different animals and is correlated with their evolutionary status. Conjugation of glutamine seems to be specific for humans and old world monkeys (James, M. O. et al., Proc. R. Soc. Lond. B. 182:25 (1972)). Systemic administration of AS2-1 to a patient produces a relative deficiency of glutamine and introduces phenylacetyglutamine which competes with glutamine.

According to the present inventor, there are three possible mechanisms of induction of terminal differentiation by AS2-1: deviation from the genetic code, modification of DNA bases and RNA editing (Burzynski, S. R., Drugs Under Exptl. Clin. Res. 16:361 (1990)).

According to the present inventor's hypothesis, TAG codon may not represent a termination codon in certain abnormal cells. According to data published by others, certain protozoa use stop codon TAG for incorporation of glutamine into polypeptide chain (Preer, J. R. et al., Nature 314:188 (1985) and Caron, F. et al., Nature 314:185 (1988)). This allows the protein synthesis to continue through incorporation of glutamine instead of stopping at stop codon. The existence of such change in the code may explain why abnormal cells are more sensitive to relative deficiency of glutamine than normal cells. Expression of such deviation in human cells may be affected by latent infection. It is important to notice that glutaminyl-tRNA synthetase will play a vital part in this mechanism (Rould, M. A. et al., *Science* 246:1135 (1989)).

Another possible mechanism of action of AS2-1 is based on modification of DNA bases in abnormal cells. During the course of cellular differentiation, the tendency could exist to eliminate methylated cytosine residues, similar to the process of elimination of 5-methylcytosine in the course of evolution (Bird, A. P., *Trends Genet.* 3:342 (1987)). The final result is that cytosine is converted into thymine. The disturbance of the differentiation process will create a situation where such exchange will not take place. CAG and CAA codons which are instrumental in incorporation of glutamine into the protein chain will remain, instead of being changed to TAG and TAA stop codons in differentiated cells. Such situation will make abnormal cells vulnerable to relative deficiency of glutamine.

A third possibility of selective inhibition of protein synthesis by AS2-1 in abnormal cells is through RNA editing. Such process has been described in protozoa and plants, as well as in mammals (Borst, P., *Annu. Rev. Biochem.* 55:701 (1986), Powell, L. M. et al., *Cell* 50:831 (1987) and Hiesel, R. et al., *Science* 246:1632 (1989) and allows a change from cytosine to uracil. This will result in stop codons UAG and UAA, instead of CAG and CAA, which were responsible for incorporation of glutamine. A disturbance of such process in abnormal cells will result in persistence of CAG and CAA codons and increased incorporation of glutamine into proteins.

SUMMARY OF THE INVENTION

The present invention provides methods for treating autoimmune diseases in humans by administering to the patient a pharmaceutical composition containing a pharmaceutically acceptable carrier and a therapeutically effective amount of a combination of

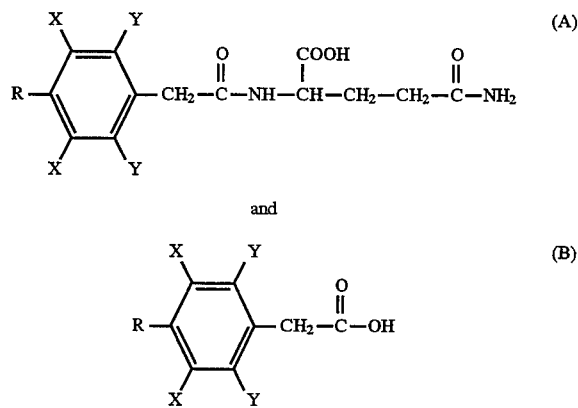

in a weight ratio ranging from about 1:1 to about 1:10 (A:B); wherein R is OH, $NH_2$, OW, or H;
X is H, F, Cl, Br, I, OH, OW, $NO_2$ or NH2;
Y is H, F, Cl, I or Br;
W is

or a $C_1$ to $C_{12}$ aliphatic group;
Z is an aliphatic or aromatic group of from $C_1$ to $C_{12}$;

X and Y can both vary within the compound; or pharmaceutically acceptable salts thereof.

As used herein, "pharmaceutically acceptable salts" mean salts having the biological activity of the parent compound and lacking unusually toxic activity at the selected administration level. Such salts include, but are not limited to, inorganic sodium, potassium and ammonium salts, organic diethanolamine, cyclohexylamine, and amino acid salts.

The pharmaceutical compositions described above exhibit significant in vivo activity in the treatment of autoimmune diseases. The term "autoimmune disease" refers to disorders wherein the immune system of a mammal mounts a humoral or cellular immune response to the mammal's own tissue or to antigenic agents that are not intrinsically harmful to the mammal, thereby producing tissue injury in such a mammal. Examples of such disorders include, but are not limited to, systemic lupus erythematosus, rheumatoid arthritis and type I diabetes. Autoimmune diseases include acute glomerulonephritis, Addison's disease, adult onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, Crohn's disease, dermatomyositis, dilated cardiomyopathy, eosinophilia-myalgia syndrome, epidermolisis bullosa acquisita (EBA), giant cell arteritis, Goodpasture's syndrome, Graves' disease, Guillain-Barré syndrome, hemochromatosis, Henoch-Schönlein purpura, idiopathic IgA nephropathy, insulin-dependent diabetes mellitus (IDDM), juvenile rheumatoid arthritis, Lambert-Eaton syndrome, linear IgA dermatosis, lupus erythematosus, multiple sclerosis, myasthenia gravis, myocarditis, narcolepsy, necrotizing vasculitis, neonatal lupus syndrome (NLE), nephrotic syndrome, pemphigoid, phemphigus, polymyositis, primary sclerosing cholangitis, psoriasis, rapidly progressive glomerulonephritis (RPGN), Reiter's syndrome, rheumatoid arthritis, scleroderma, Sjögren's syndrome, stiff-man syndrome, thyroiditis, and ulcerative colitis.

Depending on the nature of the autoimmune disease and manner in which it manifests itself (e.g. systemically or locally as with skin lesions), the pharmaceutical compositions of the present invention can be administered by using conventional modes of administration, e.g., orally, topically, parenterally, and the like. The pharmaceutical compositions of the present invention comprise a suitable pharmaceutically acceptable carrier and the combination of active phenylacetylglutamine and phenylacetate derivatives in an amount effective to ameliorate the symptoms heralding the particular autoimmune dysfunction, such as for example fatigue; inflammation; paresis, joint stiffness, pain or swelling; skin lesions or nodules; and skin discoloration.

In treatments using the pharmaceutical combination, a therapeutically effective dosage regimen should be used. Generally, in the treatment of autoimmune diseases, a proper dosage regimen requires providing the medication over a period of time to achieve noticeable therapeutic effects. As used herein, the expression "therapeutically effect amount" or dosage, or regimen means that amount, dosage or regimen which results in sufficient concentrations of the active ingredient combination at the cellular or tissue site of manifestation effective to prevent, arrest or ameliorate the symptomatic dysfunction.

A particular combination of two compounds, termed herein Antineoplaston AS2-1 (1:4 ratio of sodium salt of phenylacetylglutamine and sodium salt of phenylacetic acid) is particularly preferred and has been administered to human patients for the purpose of treating autoimmune diseases in the form of 500 mg capsules and 100 mg/ml intravenous infusions. Autoimmune diseases particularly amenable to treatments employing the present pharmaceutical composition include rheumatoid arthritis, lupus erythematosus, vasculitis, insulin dependent diabetes mellitus and multiple sclerosis.

DETAILED DESCRIPTION OF THE PREFERRED EMBODIMENTS

I. Methods of Preparing the Compounds

Desired R,X,Y substituted derivatives of phenylacetic acid can be purchased commercially or prepared synthetically by methods known to those skilled in the art according to well established rules of electrophilic and nucleophilic aromatic substitution. For example, 4-hydroxyphenylacetic acid, which is commercially available from Aldrich Chemical Company, Inc., can be nitrated with dilute $HNO_3$ to produce 4-hydroxy-3-nitrophenylacetic acid that is used as is in the next step of reaction. Alternatively, the nitro group in 4-hydroxy-3-nitrophenylacetic acid can be reduced to the corresponding amine and then reacted with sodium nitrite in acid to form the diazonium salt, that can be converted into a wide range of functional groups, including chloro, fluoro, bromo and hydroxyl. Phenylacetic acid can alternatively be nitrated in the 4-position to produce 4-nitrophenylacetic acid, that is used as is in the reaction or converted to the diazonium salt and derivatized. The nitro group can be reduced to the corresponding amino group as a final step of reaction by methods known to those skilled in the art, including catalytic hydrogenation.

The compounds of this invention can be prepared by condensation of the appropriate R,X,Y substituted phenylacetic acid derivative with L-glutamine to produce the corresponding R,X,Y substituted phenylacetylglutamine derivative. The condensation reaction can be facilitated by prior activation of the phenylacetic acid derivative with a reagent such as N-hydroxy-succinimide in the presence of DCC (N,N-dicyclohexylcarbodiimide), 2-mercaptothiazoline in the presence of DCC, or DCC alone. These reactions are described in more detail in Burzynski, *Drugs of the Future* 10(2):103 (1985).

II. Preparation of Pharmaceutical Compositions and Mode of Administration

As stated above, the combination of R,X,Y substituted phenylacetic acid and R,X,Y substituted phenylacetylglutamine of the present invention is useful in the treatment of autoimmune diseases. Pharmaceutical compositions, including these active compounds, can be prepared as described below.

Mixtures of the active compounds, or pharmaceutically acceptable salts thereof, are included in the pharmaceutically acceptable carrier or diluent in an amount sufficient to exert a therapeutic effect without serious side effect. The combination of active materials can be administered by any appropriate route, for example, orally, parenterally, intravenously, intradermally, subcutaneously, intraperitoneally, or topically, in liquid or solid form.

The concentration of active compounds in the drug composition will depend upon absorption, inactivation, and excretion rates of the active compound as well as other factors known to those skilled in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions.

The combination active ingredient may be administered at once, or may be divided into a number of smaller doses to be administered at varying intervals of time, e.g., 1 to 9 times daily, typically 4 times daily. For less advanced cases of autoimmune disease, oral treatment is effective. Typically, the patient is given the combination, such as Antineoplaston AS2-1 capsules, from 1 to 10 g/day, or 20 mg/kg/24 h to 150 mg/kg/24 h, and preferably, 6 g/day or 85 mg/kg/24 h. For advanced cases of autoimmune disease, treatment in the form of intravenous infusions is used. The dosages for the combination of sodium salt phenylacetylglutamine and sodium salt of phenylacetic acid are from 0.5 g to 60 g/day. When these inventive compositions are to be administered by the topical route, the concentration in the suspension medium can vary from 0.1 to 100 mg active ingredients/ml. A preferred concentration range lies between 0.5 and 50 mg active ingredients/ml.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, capsules, elixirs, suspensions, syrups or the like. Pharmaceutically compatible binding agents and/or adjuvant materials can be included as part of the composition.

Although not required, the combination of active ingredients may be provided in a composition that protects it from the acidic environment of the stomach. The composition can be orally administered in combination with an antacid formulation. The composition can also be administered in an enteric coating that maintains its integrity in the stomach and releases the active compounds in the intestine.

The active compounds can also be mixed with other active materials that do not impair the desired action, or with materials that supplement the desired action, including immunosuppressive or anti-inflammatory agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

If administered intravenously, preferred carriers are physiological saline, distilled sterile water, or phosphate buffered saline (PBS). For topical application, the active combination can be placed in dimethyl sulfoxide (DMSO) or in the form of ointments, creams, salves and the like.

The following examples illustrate the present invention in further detail.

EXAMPLE 1 (PATIENT: HC)

The patient is a 56-year-old white male who was complaining of morning stiffness of the joints, swelling of both wrists, metacarpophalangeal joints and proximal interphalangeal joints on both sides, rheumatoid nodules around the right wrist, difficulty walking because of pain and stiffness in the left knee. The stiffness in the morning persisted for over an hour. The patient had the above symptoms for approximately two years.

This patient was in very good health until two years ago when he developed pain and swelling in the right knee. He was receiving the treatment with nonsteroid anti-inflammatory agents, including Feldene which resulted in temporary improvement. At the same time, the patient developed symptoms in small joints of both hands. About a year ago, he had decrease of symptoms in the right knee, but began having similar symptoms in the left knee which continues at present.

The treatment with Antineoplaston AS2-1 began on Oct. 29, 1991. The patient was advised to take three capsules qid with meals (58 mg/kg/24 h).

The evaluation after eight days of treatment revealed less stiffness in the joints and significant decrease in the size of the rheumatoid nodule on the right wrist. When examined after 45 days of treatment, the patient was feeling much better. He had only slight morning stiffness in the joints, which was less than 10 minutes of duration. He did not complain of fatigue and did not have joint pain and swelling in both knees, both wrists, metacarpophalangeal joints and proximal interphalangeal joints on both sides. The rheumatoid nodule on the right wrist was smaller than on pretreatment examination. The patient continues to feel well after three months of treatment. He did not complain of stiffness and pain in the metacarpophalangeal joints and proximal interphalangeal joints on both sides. However, he still had slight pain in the right wrist and left knee, but without swelling. The follow-up examination on Apr. 1, 1992 after five months of treatment revealed the patient in good condition and feeling very well. He did not complain of any stiffness in the joints, but occasionally he had pain in the right wrist. The patient continues the treatment at present.

EXAMPLE 2 (PATIENT: KD)

The patient is a 34-year-old white female who was complaining of increased tiredness and morning stiffness of the joints, swelling and pain in both wrists and metacarpophalangeal joints in both hands, pain in the knees and the shoulders and in the affected joints in the hands and wrists.

The patient developed these symptoms approximately two and one-half years ago. Stiffness in the joints persisted usually for a number of hours every day. Two years ago, she began treatment with Naprosyn 500 mg bid which initially resulted in improvement, but after approximately nine months of treatment, the disease progressed further. Naprosyn was discontinued in September 1990 and then the patient began taking Meclomen 100 mg qid. She had improvement for five months, but after that, further worsening of the disease and decided to discontinue Meclomen. Recently, she also developed pain and swelling at the base of the neck.

Her pretreatment physical examination was positive for symmetrical swelling of both wrists and metacarpophalangeal joints and stiffness in the affected joints. She also complained of pain in both knees and shoulders and the base of the neck.

The treatment with Antineoplaston AS2-1 began on Sep. 26, 1991. The patient was advised to take three capsules qid with meals (65 mg/kg/24 h).

The patient had marked improvement after the first month of treatment. When evaluated on Oct. 30, 1991, she stated that the pain in the wrists and hands disappeared during the second week of treatment. With three and one-half weeks from starting the treatment, the pain in the hips and knees disappeared. The patient was free from pain for the first time in two and one-half years. After 42 days of treatment on Nov. 7, 1991, the patient did not report any symptoms. She did not have morning stiffness and fatigue and did not report joint pain. She did not have joint tenderness and pain on motion and no soft tissue swelling in the joints and tendon sheaths. Her physical examination was within normal limits.

EXAMPLE 3 (PATIENT: TE)

At the beginning of the treatment with Antineoplaston AS2-1, the patient was a 46-year-old white female who was complaining of occurrence of nodules located under the skin of her arms, thighs and abdomen. The nodules were painful and had purple discoloration. The patient had continuous hair loss, anemia, pain of the joints, especially knees, elbows, shoulders and small joints in the hand and feet.

This patient was in reasonable health until the spring of 1987 when she was diagnosed with lupus erythematosus with involvement of the internal organs. In 1989 after an acute stage of the disease, she developed symptoms described above and was diagnosed with small vessel vasculitis. In June 1990, the patient was treated with Dexamethasone for approximately six weeks, which resulted in improvement of vasculitis, but gave her intolerable side effects. Since then, she did not have any treatment and her disease was becoming progressively worse. The pretreatment physical examination was significant for small purple nodules located on the medial and anterior surface of both thighs and both arms, on the chest and on the back. The nodules had purple discoloration. They were firm, slightly painful and pruritic. The patient was also complaining of pain in the joints, including knees, elbows, shoulder, small joints in the hands and feet.

The treatment with Antineoplaston AS2-1 began on Apr. 22, 1991. The patient was advised to take three capsules qid with meals (100 mg/kg/24 h). On May 17, 1991, the dose was decreased to two capsules tid (50 mg/kg/24 h). The treatment was discontinued on Jun. 9, 1991.

The patient had marked and rapid improvement in her condition. On the third day of treatment, she was already feeling much better. She was not complaining of itching and pain anymore. Her physical examination revealed marked reduction of the size of the involved areas and change of color from bright red to brown. At the end of the first week of treatment, most of the nodules were no longer present. However, there were still a few nodules located on the medical surface of the left thigh. The patient continued to have further improvement and at the beginning of June 1991, she was completely free from signs and symptoms of the disease. As of the execution date of the attached declaration, Jun. 4, 1992, the patient continued to be in remission and off treatment.

EXAMPLE 4 (PATIENT: IS)

The patient is a 29-year-old white female who was diagnosed with multiple sclerosis. In March 1991, she showed symptoms of paresis of the left arm and left leg with hyperesthesia, Hofmann Trommer reflex positive left side, clonus left foot, sensory loss of the right leg up to the navel, X-skull and cervical spine: w.n.1., cerebral CT-scan: w.n.1. Therapy was begun with Serocytols (serum from horses injected with cell-preparations from sheep) and amino acids were supplemented on the basis of the amino acid analysis. After six months, she had improved much but she still complained of sensations of electrical shocks and recurrent paresis. She remained rather tired. Beginning January 1992, AS2-1 two 500 mg capsules three times daily were given. By April 1992, she was less tired, despite flu, with almost no paresthesia. As of the execution date of the attached declaration, Jun. 4, 1992, she was functioning normally, with normal reflexes and normal motor activity.

EXAMPLE 5 (PATIENT: LR)

The patient is a 34-year-old white male who was complaining of progressive weakness, occasional shortness of breath, decreased vision and decreased memory. He was in good health until July 1986 when he was diagnosed as HIV positive. He associates his infection with homosexual contact. In mid-1988, he was started on high dose AZT which was discontinued in August 1989 when the patient developed pneumocystis pneumonia. In February 1990, he began taking DDI which was discontinued after three months because of pancreatitis. Since then, he had not taken any established treatment for AIDS. The course of the disease has been complicated through the recurrent herpes labialis and genitalis, recurrent candida infection in the mouth and molluscum contagiosum. In September 1990, the patient was diagnosed with diabetes mellitus which required daily injections of insulin, usually insulin Lente 32 units daily and regular insulin 3 to 9 units daily. He neglected the daily injection of insulin in July 1991, developed acidosis and was admitted to the hospital in semicomatose state. Symptoms improved after resuming the daily injections of insulin.

The treatment with Antineoplaston AS2-1 500 mg capsules began on Nov. 13, 1991. At the beginning of treatment, the patient had CD4+ count equal to 3/mm$^3$ and CD8+ count of 215/mm$^3$. After one month of treatment on December 10, his CD4+ count increased to 10/mm$^3$ and CD8+ count to 807/mm$^3$. In the first week of March 1992, the patient developed symptoms of hypoglycemia and was advised to discontinue daily injections of insulin. Since then, he is off insulin and is free from symptoms and signs of diabetes mellitus. His decreased vision and decreased memory improved and currently the patient has perfect vision and memory.

As of the execution date of the attached declaration, Jun. 4, 1992, the treatment with Antineoplaston AS2-1 had yielded an objective improvement in AIDS and the patient appeared to be in complete remission of insulin dependent diabetes mellitus.

What is claimed is:

1. A method of treating autoimmune disease in an afflicted human host comprising:

administering to the host a pharmaceutical composition containing a therapeutically effective amount of a combination of compounds of the formula:

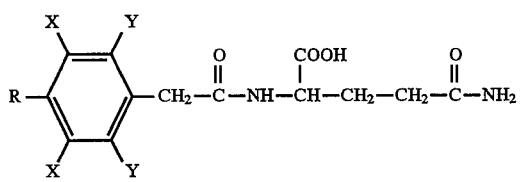

and

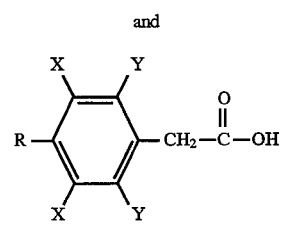

in a weight ratio ranging from about 1:1 to about 1:10 (A:B);

wherein R is OH, NH$_2$, OW, or H;

X is H, F, Cl, Br, I, OH, OW, NO$_2$, or NH$_2$;

Y is H, F, Cl, Br, or I;

W is

or a $C_1$ to $C_{12}$ aliphatic group;

Z is an aliphatic or aromatic group of $C_1$ to $C_{12}$;

X and Y can both vary within the compound; or pharmaceutically acceptable salts thereof, together with a pharmaceutical carrier.

2. The method of claim 1 wherein the pharmaceutical composition contains a mixture of phenylacetylglutamine and phenylacetic acid or pharmaceutically acceptable salts thereof.

3. The method of claim 1 wherein the pharmaceutical composition contains a 1:4 ratio of A:B.

4. The method of claim 2 wherein the pharmaceutical composition contains a 1:4 ratio of phenylacetylglutamine sodium salt and phenylacetic acid sodium salt.

5. The method of claim 1 wherein the pharmaceutical composition is administered to humans in the mount of 0.5 to 20 g/day.

6. The method of claim 1 wherein the pharmaceutical composition is administered orally, topically or parenterally.

7. The method of claim 1 wherein the afflicted host is afflicted with rheumatoid arthritis.

8. The method of claim 1 wherein the afflicted host is afflicted with necrotizing vasculitis.

9. The method of claim 1 wherein the afflicted host is afflicted with lupus erythematosus.

10. The method of claim 1 wherein the afflicted host is afflicted with multiple sclerosis.

11. The method of claim 1 wherein the afflicted host is afflicted with myasthenia gravis.

12. The method of claim 1 wherein the afflicted host is afflicted with psoriasis.

13. The method of claim 1 wherein the afflicted host is afflicted with Crohn's disease.

14. The method of claim 1 wherein the afflicted host is afflicted with Guillain-Barré syndrome.

15. The method of claim 1 wherein the afflicted host is afflicted with Addison's disease.

16. The method of claim 1 wherein the afflicted host is afflicted with ulcerative colitis.

17. The method of claim 1 wherein the afflicted host is afflicted with Graves' disease.

18. The method of claim 1 wherein the afflicted host is afflicted with insulin dependent diabetes mellitus.

19. The method of claim 1 wherein the afflicted host is afflicted with alopecia totalis.

20. The method of claim 1 wherein the afflicted host is afflicted with amyotrophic lateral sclerosis.

* * * * *